United States Patent [19]

Klein et al.

[11] Patent Number: 5,304,645
[45] Date of Patent: Apr. 19, 1994

[54] RESORUFIN DERIVATIVES

[75] Inventors: Christian Klein, Weilheim; Hans-Georg Batz, Tutzing; Rupert Herrmann, Weilheim, all of Fed. Rep. of Germany

[73] Assignee: Boehringer Mannheim GmbH, Mannheim, Fed. Rep. of Germany

[21] Appl. No.: 758,288

[22] Filed: Mar. 28, 1991

Related U.S. Application Data

[60] Continuation of Ser. No. 504,323, Apr. 3, 1990, abandoned, which is a division of Ser. No. 889,676, Jul. 24, 1986, Pat. No. 4,954,630.

[30] Foreign Application Priority Data

Jul. 25, 1985 [DE] Fed. Rep. of Germany ....... 3526565

[51] Int. Cl.$^5$ ................. A61K 31/435; A61K 31/495
[52] U.S. Cl. ................................... 544/10.2
[58] Field of Search ........................................ 544/102

[56] References Cited

U.S. PATENT DOCUMENTS

| | | | |
|---|---|---|---|
| 4,141,688 | 2/1979 | Morris et al. | 23/230 |
| 4,667,032 | 5/1987 | Lau et al. | 544/35 |
| 4,859,667 | 8/1989 | Lau et al. | 544/102 |
| 4,900,822 | 2/1990 | Eltz et al. | 544/102 |
| 4,954,630 | 9/1990 | Klein et al. | 544/102 |
| 5,242,805 | 9/1993 | Naleway et al. | 435/18 |

FOREIGN PATENT DOCUMENTS

| | | |
|---|---|---|
| 2834743 | 2/1979 | Fed. Rep. of Germany . |
| 807687 | 1/1959 | United Kingdom . |

OTHER PUBLICATIONS

Ried, W., et al. (1972) Liebigs Ann. Chem. 764:11–20.
Bird, C. W., et al. (1979) Tetrahedron 36:529–533.

Primary Examiner—Nicholas S. Rizzo
Attorney, Agent, or Firm—Felfe & Lynch

[57] ABSTRACT

The present invention provides resorufin derivatives of the general formulae:

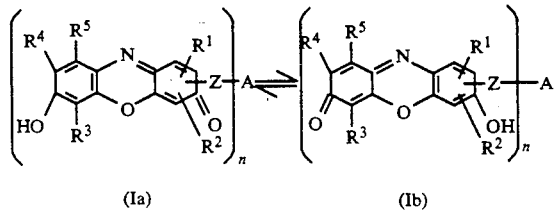

(Ia)   (Ib)

wherein $R^1$, $R^2$, $R^3$, $R^4$ and $R^5$, which can be the same or different, are hydrogen, halogen, carboxyl, carboxamido, lower alkoxycarbonyl, cyano or nitro groups or lower alkyl or lower alkoxy radicals, which can be substituted by carboxyl, carboxamido, lower alkoxycarbonyl, cyano or nitro groups, and wherein $R^4$ and $R^5$ can together also represent an anellated aromatic residue, Z is a bridge member, A is the residue of a ligand and n is a whole number of from 1 to 200.

The present invention also provides processes for the preparation of these resorufin derivatives, as well as intermediates for the preparation thereof.

8 Claims, 1 Drawing Sheet

RESORUFIN DERIVATIVES

This application is a continuation of application Ser. No. 07/504,323 now abandoned, filed Apr. 3, 1990 which is a division of Ser. No. 06/889,676 filed Jul. 24, 1986, now U.S. Pat. No. 4,954,630.

Figure 1:
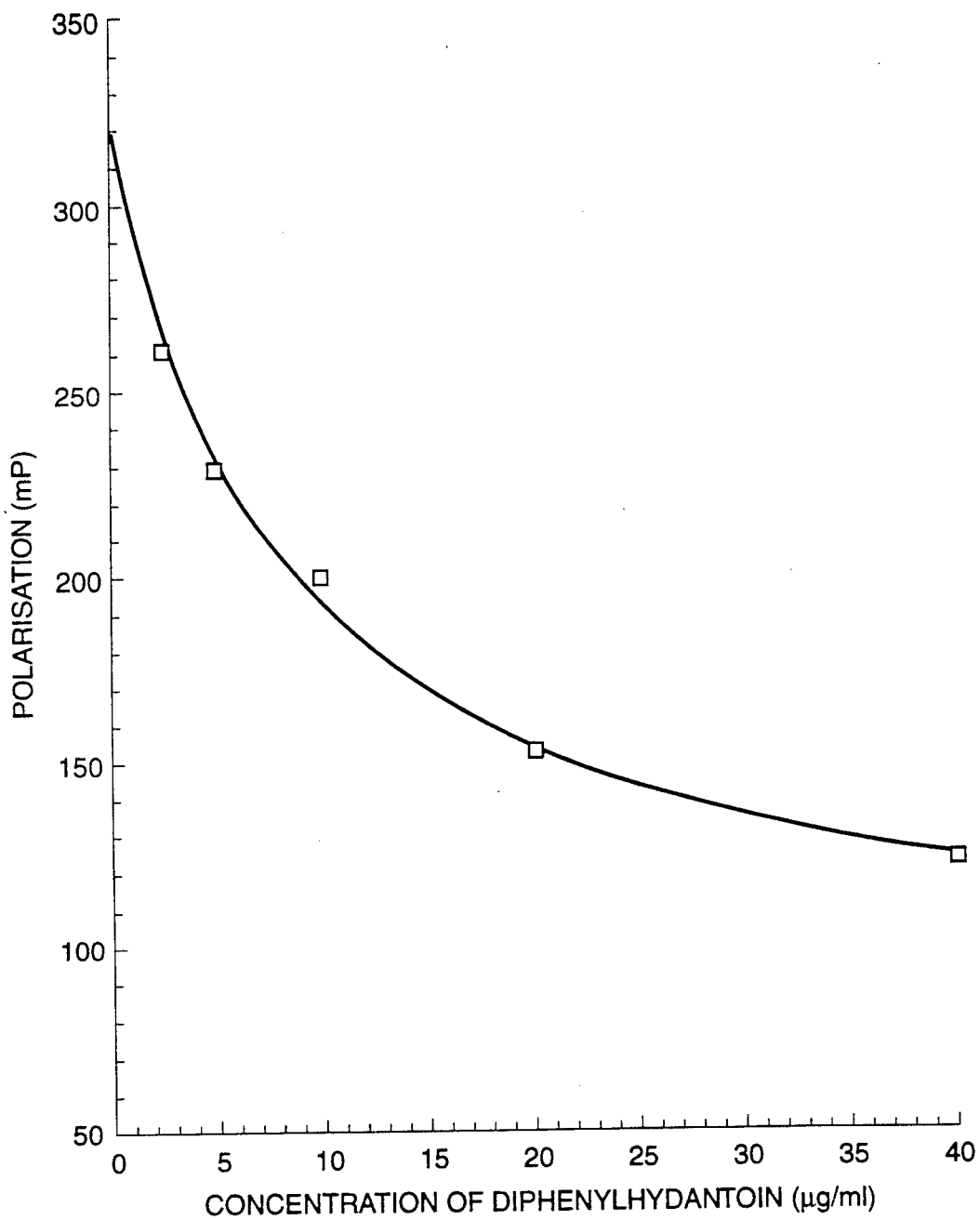
FIG. 1 shows diphenylhydantoin concentrations of the samples (μ/ml) as plotted against the measured polarization values (mp).

The present invention is concerned with resorufin derivatives, which can be used as fluorescent-labelled low or high molecular weight compounds, as well as with a process for the preparation thereof.

Fluorescing compounds are widely used as labelled compounds in chemical and biological processes, for example in clinical analyses but also in increasingly new fields, because of their ability to emit certain wavelengths after excitation. In biochemistry, fluorescent coloured materials are increasingly used as highly sensitive labellings. There are thereby used not only compounds of fluorescent coloured materials with low molecular weights but also high molecular weight substances. As examples of the wide field of use of such fluorescent conjugates, there may be mentioned:

Fluorescence immunoassays for which there is used a hapten, antigen or a specific antibody labelled with a fluorescent coloured material. Due to the specific binding of the antibody to the hapten or antigen, the concentration of these materials or of the antibody can be determined according to various processes.

In immunofluorescent microscopy, antigens, for example whole cells or proteins, are made visible under the microscope by fluorescent-labelled antibodies (see Wang et al., Meth. Enzymology, 85, 514 et seq.).

The distribution of a hapten or antigen in a cell can also be observed directly when the compound in question is introduced into the cell in fluorescent labelled form and monitored under a microscope.

Fluorescent-labelled latex particles are used in the sorting of cells in a "fluorescent activated cell sorter" (FACS).

Not least, substrates which carry a fluorescing labelling serve for the determination and measurement of the activity of enzymes.

Competitive immunoassays are based on the competition between a ligand to be determined in a sample and a labelled ligand present in known concentration for a known but limited number of ligand binding points on antibodies which are specific not only for the ligand to be determined but also for the labelled ligand. The concentration of the ligand to be determined in the sample is decisive for how many labelled ligand molecules are bound to the antibodies. The concentration of complexes of antibodies and fluorescent-labelled ligands can be determined by spectroscopic methods. It is inversely proportional to the ligand concentration to be determined present in the sample. As labelled ligands which are added in known concentration to the sample with the ligands to be determined, there were originally preponderantly used ligands labelled with radioisotopes. Because of the known disadvantages of a radioisotope labelling, labelling with fluorescent compounds is achieving ever more importance. Fluorescing compounds are hereby bound to the molecules of the substance to be determined. These conjugates can then, in principle, be used for the most varied fluorescence immunoassays, for example fluorescence polarisation immunoassay, fluorescence quenching immunoassay and fluorescence enhancement immunoassay.

As labellings, there can, in principle, be used all fluorescing coloured materials which possess a large extinction coefficient and a high quantum yield, as well as a sufficient stability under the test conditions. Hitherto, there were, therefore, used fluorescein or fluorescein derivatives (see J. Landon and R. S. Kamel in Immunoassays 80s, Univ. Park Press, Baltimore, Md., 1980, pp. 91–112). However, high or low molecular weight compounds labelled with fluorescein or derivatives thereof have disadvantages. Absorption and emission maxima of the fluorescein-labelled substances lie in a wavelength range of from 490 to 520 nm. Since a considerable number of analytical methods and especially fluorescent immunoassay processes, is carried out in body fluids, such as serum, in the said spectral range, disturbances occur due to the inherent fluorescence of biological materials in the samples. Bilirubin, which also absorbs light in the region of about 500 nm and emits fluorescence, is mainly responsible for this.

Some measurement arrangements require labelling substances with a Stokes shift which is as great as possible. In the case of fluorescein derivatives, this shift is at most 30 nm. This gives rise to light scattering problems which impair the sensitivity of the fluorescence measurements. For such cases, compounds with a greater Stokes shift than that of the fluorescein derivatives would be desirable.

Therefore, it is an object of the present invention to provide compounds which no longer display these disadvantages. This object is achieved by the provision of the resorufin derivatives according to the present invention.

Thus, according to the present invention, there are provided resorufin derivatives of the general formulae:

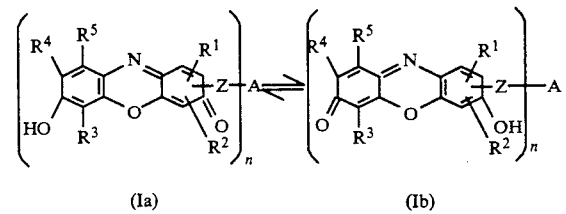

(Ia)  (Ib)

wherein $R^1$, $R^2$, $R^3$, $R^4$ and $R^5$, which can be the same or different, are hydrogen, halogen, carboxyl, carboxamido, lower alkoxycarbonyl, cyano or nitro groups or lower alkyl or lower alkoxy radicals, which can be substituted by carboxyl, carboxamido, lower alkoxycarbonyl, cyano or nitro groups, and wherein $R^4$ and $R^5$ can together also represent an anellated aromatic residue, Z is a bridge member, A is the residue of a ligand and n is a whole number of from 1 to 200.

The lower alkyl and lower alkoxy radicals in the definitions of $R^1$, $R^2$, $R^3$, $R^4$ and $R^5$ contain hydrocarbon chains with up to 5 and preferably up to 3 carbon atoms, the methyl, ethyl, methoxy and ethoxy radicals being especially preferred.

Halogen in the definitions of $R^1$, $R^2$, $R^3$, $R^4$ and $R^5$ means fluorine, chlorine, bromine or iodine, chlorine and bromine being especially preferred.

The anellated aromatic residue possibly formed by $R^4$ and $R^5$ is preferably benzene or naphthalene, benzene being especially preferred. The said aromatic residues can be unsubstituted or can each carry one or more substituents selected from $SO_3H$, COOH and $C_1$-$C_5$-alkoxy.

The bridge member Z is formed by conventional addition or condensation reactions between a reactive substituent $X^1$ of the resorufin basic structure and a reactive group $X^2$ of the ligand or ligand analogon, optionally with the insertion of a bifunctional compound $X^3$-M-$X^4$, wherein $X^3$ and $X^4$ are reactive groups and M the remaining part of the molecule.

In the following Table 1, there are set out, by way of example, some possible meanings for such reactive substituents $X^1$ and $X^2$ as well as the bridge members Z resulting in the case of the reaction.

TABLE 1

Some meanings of the reactive groups $X^1$ and $X^2$ and the bridge members Z resulting therefrom

| $X^1$ | $X^2$ | Z |
|---|---|---|
| —COOH | —NH$_2$ | —CONH— |
| —COOT* | —NH$_2$ | —CONH— |
| —COOCO$_2$T$^{1}$** | —NH$_2$ | —CONH— |
| —NCO | —NH$_2$ | —NHCONH— |
| —NCS | —NH$_2$ | —NHCSNH— |
| —NH—(triazinyl-Cl) | —NH$_2$ | —NH—(triazinyl-NH—) |
| —HC=CH—CO— | —SH | —S—CH(—)—CH$_2$—CO— |
| —CHO | —NH$_2$ | —CH=N— |
| —SO$_2$Cl | —NH$_2$ | —SO$_2$NH— |
| —COCH$_2$-halogen | —SH | —COCH$_2$—S— |
| —COCH$_2$-halogen | —OH | —COCH$_2$—O— |
| —(CH$_2$)$_m$—NH$_2$*** | —COOH | —(CH$_2$)$_m$—NH—CO— |
| —CO—N(piperazinyl)—COOT* | —NH$_2$ | —CO—N(piperazinyl)—CO—NH— |

*T is an alkyl radical with up to 5 carbon atoms or an electronegatively-activated ester group, for example an N-hydroxysuccinimide ester group.
**$T^1$ is an alkyl radical with up to 5 carbon atoms.
***m is 0 or a whole number of from 1 to 3.

Instead of primary amines such as are set out in Table 1, as reactive groups $X^1$ and $X^2$ there can also be used, in the same way, secondary amines with the formation of corresponding products.

As bifunctional compounds $X^3$-M-$X^4$, there may be mentioned diamines, dicarboxylic acids, as well as derivatives thereof, dialdehydes, aminocarboxylic acids and further compounds which are conventionally used for the production of such linkages. Examples of such compounds include piperazine, 1,2-ethylenediamine, succinic acid, glutaric dialdehyde, glycine, sarcosine, β-alanine and piperidine-4-carboxylic acid.

By a ligand in the definition of A, there are to be understood haptens, antigens, antibodies and substrates, as well as carriers and compounds derived therefrom.

By a hapten, according to the present invention there is to be understood a substance with a low molecular weight which, as a rule, is not able to produce antibodies. Compounds with a molecular weight of from about 100 to about 2000 are to be regarded as being substances with a low molecular weight. Examples of such substances include physiologically-active substances which are present in the mammalian or human organism, as well as metabolites thereof and pharmaceutical substances which are administered to animals and humans, as well as metabolites thereof. However, by the term hapten there can also be understood all further low molecular weight compounds insofar as they only have a molecular weight in the above-mentioned range. Examples of possible haptens include amines, steroids, hormones, carbohydrates, peptides, oligonucleotides, combinations thereof and the like.

Antigens are high molecular weight compounds which are usually able to produce antibodies in organisms treated therewith. According to the present invention, high molecular weight compounds are those which have a molecular weight of at least about 2000 but preferably, however, a molecular weight of at least about 5000. The molecular weight of such compounds cannot be upwardly limited. The value can amount to up to 20 million but can also be greater than that. Antigens which can be present as ligands in compounds of general formulae (Ia) and (Ib) include, for example, proteins, nucleic acids, polysaccharides, combinations thereof and other high molecular weight substances. According to the present invention, the term antigen is to be understood to mean all high molecular weight compounds which have a minimum molecular weight of about 2000.

Antibodies are all those proteins or glycoproteins which react specifically with antigens or haptens, as well as with compounds derived therefrom, to form a complex. According to the present invention, as ligands in compounds of general formulae (Ia) and (Ib), there can be used intact antibodies as well as fragments thereof. According to the present invention, these fragments can also be called antibodies insofar as they are able to bind antigens and haptens, as well as compounds derived therefrom.

The present invention also provides a process for the preparation of the compounds according to the present invention of general formulae (Ia) and (Ib). According to this process, compounds of the general formulae:

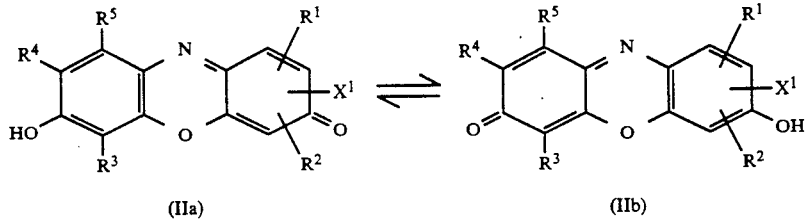

By substrates there are to be understood compounds which undergo a detectable change in a chemical reaction. For example, amongst these are to be understood all those compounds or materials derived therefrom upon which enzymes act, for example amino acids, peptides, proteins, glycosides, oligo- and polysaccharides, nucleotides, nucleic acids and combinations thereof and other enzymatically changeable substances.

Carriers can be naturally-occurring or synthetic, cross-linked or non-cross-linked materials with or without a definite shape. Hereunder are to be understood individual compounds or mixtures of compounds. As carriers, there can be used, for example, compounds or mixtures of compounds, for example polysaccharides, nucleic acids, peptides, proteins and combinations thereof, as well as rubber, lignin, glass, charcoal, synthetic addition and condensation polymers, such as polystyrene, polyacrylics, vinyl compounds, polyesters, polyethers and polyamides, and also complex structures, such as latex particles, vesicles, liposomes, cell wall parts or even whole cells.

A compound derived from a particular ligand is referred to as a ligand analogue. A ligand analogue is to be understood to be a substance which structurally differs only slightly from the corresponding ligand but, with regard to its properties, displays no significant difference. The difference can be due, for example, to an additional substituent or to a missing part of the molecule.

In principle, all ligands can be used for the formation of the compounds (Ia) and (Ib) according to the present invention which carry free amino, hydroxyl, sulphhydryl or carboxyl groups via which the ligands can be attached to the resorufin basic structure, possibly with the insertion of a bridge member. Free amino or carboxyl groups are especially advantageous. Free amino groups are to be understood to be not only primary but also secondary amino groups. If the ligands do not possess suitable groups, then such groups, for example amino or carboxyl groups, must be introduced by synthetic means. Furthermore, it is possible chemically to activate non-reactive functional groups of such ligands possibly present. Since the thus resulting substances are no longer completely identical with the original compounds, they are referred to as ligand analogues.

The number n indicates how many resorufin molecules are attached to a ligand or a ligand analogue. This number depends upon the number of reactive groups in the appropriate ligand or ligand analogue. The more reactive groups the ligand or ligand analogue possesses, the more resorufin molecules can be bound. The number n is usually from 1 to 200 and is especially preferably from 1 to 100.

wherein $R^1$, $R^2$, $R^3$, $R^4$ and $R^5$ have the same meanings as in general formulae (Ia) and (Ib) and $X^1$ is a reactive group, are reacted a) with a ligand of the general formula:

wherein $X^2$ is a reactive group and A is the residue of the ligand; or b) with a bifunctional compound of the general formula:

in which $X^3$ and $X^4$ are reactive groups and M is the residue of the bifunctional compound, and with a ligand of the general formula:

in which $X^2$ and A have the same meanings as above, whereby possibly in the case of individual process steps, protective groups are introduced and subsequently again split off and also individual reactive groups $X^1$, $X^2$, $X^3$ and $X^4$ can be converted into other reactive groups.

By reactive groups in the definitions of $X^1$, $X^2$, $X^3$ and $X^4$ there can, in principle, be understood all conventional reactive functional groups. Especially preferred functional groups include acid residues, such as carboxylic and sulphonic acids, as well as groups derived therefrom, such as esters, amides, anhydrides, acid halides, and residues such as primary or secondary amine, cyanate, isocyanate, thiocyanate, isothiocyanate, aldehyde, sulphhydryl, hydroxyl and α-ketohalide radicals and the like. Examples of reactive groups are set out above in Table 1 under $X^1$ and $X^2$. These residues can, of course, be exchanged for one another and can also assume the meanings of the reactive groups $X^3$ and $X^4$.

By the residue M of the bifunctional compound (IV), there can, in principle, be understood any organic or inorganic residue. However, those residues are preferred in which M is a straight-chained or branched, aliphatic, cycloaliphatic or aromatic residue or a combination of such residues. Especially preferred are aliphatic residues containing up to 10 and preferably up to 7 carbon atoms or those residues which include both or only one of the two reactive groups $X^3$ and $X^4$ in a cycloaliphatic residue.

Compounds of general formulae (IIa) and (IIb) are advantageously obtained from nitrosoresorcinol derivatives of the general formula:

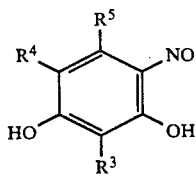

(V)

wherein $R^3$, $R^4$ and $R^5$ have the meanings given in general formulae (Ia) and (Ib), by reaction with resorcinol derivatives of the general formula:

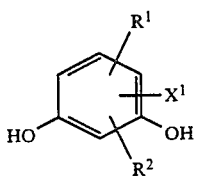

(VI)

wherein $R^1$ and $R^2$ have the meanings given in general formulae (Ia) and (Ib) and $X^1$ is a reactive group.

The reaction of compounds of general formula (V) with those of general formula (VI) preferably takes place in the presence of pyrolusite and sulphuric acid at a low temperature. Resazurin derivatives are thereby first formed which can easily be converted into resorufin derivatives of general formulae (IIa) and (IIb).

The reaction of compounds of general formula (V) with compounds of general formula (VI) is usually carried out at a temperature of from $-10°$ to $+50°$ C. and preferably of from $0°$ to $30°$ C. The reaction takes place especially gently when the compounds of general formulae (V) and (VI) are mixed at about $0°$ C. and the reaction mixture is subsequently allowed to warm up to ambient temperature. The concentration of the pyrolusite is preferably from 0.5 to 5 and more preferably from 1 to 2 mole/liter. The sulphuric acid concentration should be from 0.5 to 5 and preferably from 1 to 3 mole/liter.

The reduction of the initially formed resazurin derivatives to resorufins of general formulae (IIa) and (IIb) is preferably carried out in ammoniacal solution with zinc dust (cf. Nietzki et al., Ber. Dtsch. Chem. Ges., 22, 3020/1889) or with sodium borohydride. As solvent, there is preferably used a water-alcohol mixture and preferably a mixture of 1 part of water with 0 to 4 parts of methanol. Per mole of substance to be reduced, there are added 1 to 20 and preferably 1 to 5 mole of zinc dust or sodium borohydride. The temperature of the reaction solution is thereby maintained at $-10°$ to $+35°$ C. and preferably at $+5°$ to $+10°$ C. The exact maintenance of the temperature range has proved to be necessary for a definite course of the reaction. Without cooling, the exothermal reaction gives rise to by-products which are difficult to separate.

Under the selected mild conditions, the reaction between the compounds of general formulae (V) and (VI) takes place unambiguously and with good yield. The selected synthesis route is capable of variation. This opens up numerous possibilities of synthesis, especially having regard to the preparation of asymmetrically substituted resorufin derivatives. Due to this preparation process which is capable of many variations, a large number of resorufin-labelled compounds can be obtained, which cover a wide colour range due to their different substituents in various positions in the chromophore.

Before the reaction of the resorufin derivatives of general formulae (IIa) and (IIb) with compounds of the general formula (III) or with compounds of the general formulae (IV) and (III), the former are preferably converted into triacyldihydroresorufin derivatives of the general formula:

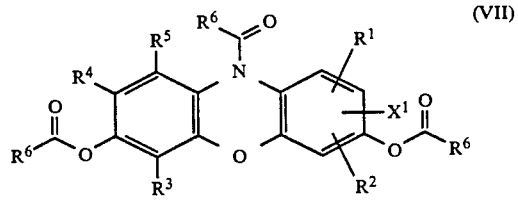

(VII)

wherein $R^1$, $R^2$, $R^3$, $R^4$, $R^5$ and $X^1$ have the meanings given in general formulae (IIa) and (IIb) and $R^6$ is a lower alkyl, aryl or aralkyl radical.

Lower alkyl in the definition of $R^6$ means an alkyl radical containing up to 5 and preferably up to 3 carbon atoms, the methyl and ethyl radicals being especially preferred. As aryl radical, the phenyl radical is especially preferred. The aralkyl radical preferably contains a phenyl radical as the aryl moiety and the alkyl moiety contains up to 5 and preferably up to 3 carbon atoms. The aralkyl radical is preferably a benzyl radical.

For the preparation of the triacyl derivatives of general formula (VII), the corresponding resorufin derivatives of general formulae (IIa) and (IIb) are first reduced with a strong reducing agent, for example stannous chloride or chromic acetate, or electrochemically. For the reduction, the resorufin derivative is heated for from 10 to 60 minutes with 2 to 10 and preferably with 2 to 6 equivalents of reducing agent in an appropriate solvent, preferably with stannous chloride in 5 to 35% aqueous hydrochloric acid. Upon cooling, the dihydro compound precipitates out. The acylation takes place in the usual manner with an appropriate acylation agent, for example acetic anhydride, benzoyl chloride or the like. The compounds of general formula (VII) are preferably prepared in a one-pot process by reductive acylation of the resorufin derivatives (IIa) and (IIb). For this purpose, the appropriate resorufin derivative is heated under reflux with 2 to 6 equivalents of reducing agent for 5 to 180 minutes in the presence of the acylation agent in an appropriate solvent or is stirred at ambient temperature for from 4 to 16 hours.

The reactive group $X^1$ in the triacyldihydroresorufin derivatives (VII) obtained can possibly be converted into another reactive group before the further reaction. Especially when $X^1$ is a carboxyl group, it is preferable to convert this into a carboxylic acid chloride, carboxylic acid anhydride or reactive ester function. This can take place in a large variety of ways, for example with carbodiimides, alcohols, halides, N-hydroxysuccinimide or the like. Numerous processes are known from the literature. Especially preferred is the conversion of the carboxylic acid function into a carboxylic acid chloride, for example with thionyl chloride/dimethylformamide, or oxalyl chloride/dimethylformamide, as well as into an activated ester, for example with a N-hydroxysuccinimide ester.

If the ligands or ligand analogues possess free amino, hydroxyl or sulphhydryl groups, then these can react as reactive groups $X^2$. The ligands or ligand analogues $X^2$-A can then be reacted directly with compounds (IIa) and (IIb), possibly after previous conversion into triacyldihydroresorufin derivatives and/or after activation of the group $X^1$ with the formation of amide, ester or thioester compounds. Because of their stability, the formation of at least one amide bond is especially preferred, whereby, for the formation thereof, it is preferable to start from compounds of general formulae (IIa)/(IIb) or (VII), wherein $X^1$ is a carboxylic acid halide group. The reaction thereof with an amino group-containing ligand or ligand analogue takes place according to conventional methods, for example in an organic solvent, such as dichloromethane, with the addition of a tertiary amine, such as triethylamine, as base. Depending upon the size of the ligand or ligand analogue and thus consequently upon the number of its free amino groups and of the amount used of compounds (IIa)/(IIb), several chromophores can be bound per ligand or ligand analogue molecule.

If, for the preparation of the compounds of general formulae (Ia) and (Ib) according to the present invention, there are used triacyl derivatives of general formula (VII), then, after the reaction, the acyl radicals of the dihydroresorufin used as protective groups must be selectively split off and the resultant leuko coloured material residue oxidised to the chromophore of the compound (Ia)/(Ib).

The O-acyl radicals of the dihydroresorufin moiety are split off especially advantageously by reaction with 2 to 10 mole and preferably with 2 to 4 mole of sodium sulphite in a mixture of water and a water-soluble solvent, for example 1,4-dioxan, methanol or ethanol and preferably water/1,4-dioxan (1:1 v/v). The reaction temperature can be from 20° to 100° C. and preferably from 80° to 100° C. N-Acyldihydroresorufin derivatives can be prepared in high yields under these reaction conditions.

The oxidation of the dihydroresorufin to give compounds of general formulae (Ia) and (Ib) can be carried out with mild oxidation agents. It is preferred to use potassium ferricyanide which is employed in 2 to 6 and preferably in 2 to 4 molar excess with regard to the leuko coloured material in a mixture of water and a water-soluble solvent, for example 1,4-dioxan, methanol or ethanol and preferably in water/methanol (3:1 v/v). The reaction is preferably carried out in the presence of an adjuvant base, for example sodium hydrogen carbonate or sodium carbonate. The reaction temperature is from 10° to 40° C. and preferably ambient temperature.

The selective splitting off of the protective N-acyl radical and the oxidation of the dihydroresorufin moiety can take place especially advantageously in a one-pot reaction. For this purpose, the N-acylated dihydroresorufin in water/methanol (3:1 v/v) is first mixed with 2 to 4 mole sodium hydrogen carbonate and an equimolar amount of 1N aqueous sodium hydroxide solution and subsequently with a 2 to 4 mole excess of potassium ferricyanide. After a period of from about 10 to 120 minutes and preferably of 30 minutes at ambient temperature, the reaction is complete.

In some cases, it is preferable not to attach the compounds (IIa)/(IIb) directly to the ligand or ligand analogue (III) but rather to introduce a spacing grouping $X^3$-M-$X^4$. As spacer, there can be used all compounds with at least two reactive groups which are conventionally employed for this purpose, diamines and aminocarboxylic acids being especially preferred for this purpose. The choice depends upon the nature of the functional groups $X^1$ and $X^2$ which are to be attached with the spacer.

The compounds which result by the reaction of resorufin derivatives of the general formulae (IIa)/(IIb) with bifunctional compounds of general formula (IV) in one or more steps, for example via compounds of general formula (VII), can be represented by the following general formulae:

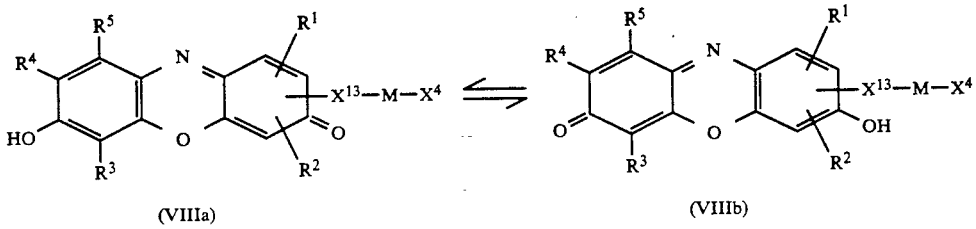

(VIIIa)  (VIIIb)

wherein $R^1$, $R^2$, $R^3$, $R^4$ and $R^5$ have the same meanings as in general formulae (Ia) and (Ib), M and $X^4$ have the same meanings as in general formula (IV) and $X^{13}$ is a functional group resulting from the reaction of $X^1$ and $X^3$.

Functional groups $X^{13}$ can be all conceivable groups resulting from the reaction with one another of the reactive residues $X^1$ and $X^3$, preferred groups $X^{13}$ including amides, thioethers, ethers, secondary and tertiary amines, as well as urea and thiourea groups.

If, in general formulae (IIa)/(IIb) and (VII), $X^1$ is a carboxylic acid function or a reactive group derived therefrom and if the reactive groups $X^2$ of the ligand or ligand analogue are amino, hydroxyl or sulphhydryl groups, then it is preferable to select a spacer $X^3$-M-$X^4$ in which $X^3$ is an amino group and $X^4$ is a carboxylic acid function or a reactive derivative thereof. The amino end can be attached to the carboxylic acid function of the compounds (IIa)/(IIb) or (VII) and the carboxyl end to the ligand or ligand analogue $X^2$-A. If, however, not only $X^1$ but also $X^2$ are both carboxylic acid functions or activated derivatives derived therefrom, then diamines have proved to be useful as spacers.

The reaction of resorufin derivatives of general formulae (IIa) and (IIb) with a bifunctional spacer groupmulae (IV) and the ligand or ligand analogue (III) advantageously takes place in two steps. First, the compounds (IIa)/(IIb), possibly after previous conversion into the active compounds (VII), are attached to the spacer (IV). The derivatives resulting herefrom can be reacted in a second step with the ligands or ligand analogues (III). The opposite method of proceeding can, of course, also be used in which, in a first step, the spacer (IV) is attached to the ligand or ligand analogue (III) and the product obtained then reacted in a second step with the resorufin derivative (IIa)/(IIb) or the activated compound (VII).

As aminocarboxylic acids, it is preferred to use amino acids, glycine, alanine, sarcosine and piperidine-4-carboxylic acid having proved to be especially useful. The coupling of resorufin derivatives of general formulae (IIa)/(IIb) or (VII) with aminocarboxylic acids with the formation of an amide bond takes place by methods which are well known. For this purpose, it is especially advantageous to use the methyl or tert.-butyl esters of the appropriate amino acids. After amide formation has taken place, protective groups which have possibly been previously introduced are selectively split off according to known methods. If, for example, an activated derivative (VII) is reacted with a carboxy-protected aminocarboxylic acid, then it is necessary selectively to hydrolyse the O- and N-acyl groups, again to oxidise the leuko coloured material to the resorufin system and subsequently to split off the carboxyl protective group of the bond aminocarboxylic acid under conventional conditions and preferably with trifluoroacetic acid. The free carboxyl group can then be activated for the conjugation of a ligand or ligand analogue (III) in an appropriate manner such as has been described for resorufin derivatives of general formulae (IIa) and (IIb). The carrying out of the conjugation itself also takes place in a manner analogous to that which has been described for the direct conjugation of ligands or ligand analogues to resorufin derivatives of general formulae (IIa) and (IIb).

In the case of ligand or ligand analogues containing carboxyl groups, it is preferable to convert resorufin derivatives of general formulae (IIa)/(IIb) or (VII) into amino group-containing compounds which can then be reacted with the carboxylic acid group-containing ligands or ligand analogues. For this purpose, it has proved to be especially simple and advantageous to react compounds of general formulae (IIa)/(IIb) or (VII) with diamines (general formula (IV) in which $X^3$ and $X^4$ are amino groups). Preferred diamines in this sense include, for example, piperazine, 1,2-diaminoethane and 1,3-diaminopropane.

The conversion of resorufin derivatives of general formulae (IIa)/(IIb) or (VII) with diamines into derivatives with free amino groups takes place according to well known methods. In order to achieve especially high yields of monosubstituted diamines, those diamines are preferably reacted which only have one reactive amino group, the second functional group being blocked by a protective group. In principle, all conventional amino protective groups can be used which can be split off again without impairment of the amide bonds, the use of tert.-butoxycarbonyl and benzoyloxycarbonyl protective groups having proved to be especially advantageous.

After the reaction of mono-protected diamines with resorufin derivatives of general formulae (IIa)/(IIb) or (VII), protective groups which have possibly been introduced are split off again and a leuko coloured material which is possibly formed as an intermediate is oxidised to the resorufin system. The splitting off of the amino protective groups of the bound diamine hereby takes place under conventional conditions and preferably with trifluoroacetic acid.

The amino group-containing resorufin derivatives thus obtained can be conjugated in conventional manner with ligands or ligand analogues (III) which, as reactive groups $X^2$, contain carboxyl groups. These carboxyl groups are advantageously activated. This can take place in the above-described manner. It is preferred to use ligands or ligand analogues of general formula (III) in which $X^2$ is activated ester groups, N-hydroxysuccinimide esters having proved to be especially advantageous. The carrying out of the conjugation itself takes place, in principle, analogously to the procedure described above for the direct conjugation of resorufin derivatives with ligand or ligand analogues, taking into account the changed roles of the functional groups.

The further reaction of the products which are obtained after the linking of resorufin derivatives (IIa)/(IIb) or (VII) with an intermediate member $X^3$-M-$X^4$ of general formula (IV) with low molecular weight ligands $X^2$-A, for example haptens, preferably takes place in a mixture of water or buffer and a water-soluble solvent, for example 1,4-dioxan, methanol or ethanol, a mixture of 0.1M potassium phosphate buffer (pH 8.5)/1,4-dioxan in a ratio of 1:1 v/v being preferred. It is possible to monitor the course of the reaction by thin layer chromatography. The reaction period can be from 1 to 24 hours but the reaction is usually completely finished after 1 to 18 hours.

For the reaction of resorufin derivatives (IIa)/(IIb), (VII) or (VIIIa)/(VIIIb) with high molecular weight ligands of general formula (III), N-hydroxysuccinimide esters prove to be especially advantageous. Thus, for example, in the case of the coupling of rabbit IgG, even 6 mole of resorufin derivative per mole of IgG suffice in order to achieve a degree of labelling of 3 molecules of resorufin per mole IgG. The previously used fluorescent coloured materials for this purpose, which display a maximum absorption wavelength of $\lambda_{max} > 470$ nm, contain, as reactive group, an isothiocyanate or sulphonic acid chloride residue, for example fluorescein isothiocyanate or Texas Red. In these cases, for coupling to rabbit IgG, there must be used a substantially greater colouring material excess in order to achieve the same degree of labelling.

The conjugation of high molecular weight compounds of general formula (III), for example of proteins, preferably takes place in a buffer and especially advantageously in 0.1M potassium phosphate buffer (pH 8.0 to 9.0) when the reactive group $X^1$ or $X^2$ is an N-hydroxysuccinimide ester. The reaction temperature can be from 10° to 35° C., the reaction preferably being carried out at ambient temperature.

Because of their especially good spectral properties, the present invention is also concerned with the use of the compounds of general formulae (Ia) and (Ib) according to the present invention in analytical processes in which a fluorescent property of the compounds of general formulae (Ia)/(Ib) or of a reaction product thereof is measured.

In heterogeneous immunoassays, a separation of ligands bound to antibody and free ligands by precipitation with appropriate substances or by the use of antibodies bound to solid carriers is necessary before the concentration of free or bound ligands is determined. In homogeneous immunoassays, the investigation of the antibody-ligand complex formation in the sample takes place without such a separation. The homogeneous immunoassay methods include, for example, fluorescence quenching, fluorescence enhancement and fluorescence polarisation methods, in which fluorescing substances are used as labelling agents. Especially the last-mentioned method suffers from the disadvantages mentioned initially of the fluorescence labelling conventionally used. Since the compounds of general formulae (Ia) and (Ib) according to the present invention possess absorption and emission maxima which lie far outside those of biological materials in body fluids which disturb due to their inherent fluorescence, they are especially useful in fluorescence polarisation immunoassays (FPIA). A further advantage of the compounds according to the present invention is that, in the case of appropriate substitution, they display an especially high Stokes shift of up to about 70 nm.

The FPIA processes are, in principle, based on the principle of conventional fluorescence immunoassays.

If appropriately fluorescence-labelled ligands are excited to fluoresce with linear polarised light, then, on the basis of the small time delay between excitation and emission, the molecule rotates before it emits radiation. In this way, the plane of the linear polarised light is also rotated through a definite angle. A number of molecules can, within this short period of time, lead to a certain depolarisation of the fluorescence emission due to rotation diffusion. For the polarisation of the emitted fluorescence, it is the greater the greater is the molecule and consequently the slower is the rotation. This association can be utilised for the measurement of the binding of ligands to antibodies since free, labelled ligands possess a smaller molecular volume than complexes of labelled ligands bound to antibodies. The polarisation is inversely proportional to the ligand concentration to be determined and present in the sample.

The concentration of the labelled ligand or ligand analogue and of the antibody necessary for such immunological processes depends upon the measurement apparatus used, as well as upon the particular characteristic properties of the labelled ligand or ligand analogue used and of the antibody itself. In principle, these concentrations naturally also depend upon the concentration of the ligand to be determined and must, therefore, be empirically ascertained. This ascertainment can be made by simple optimisation.

The ligand concentration which is to be determined generally varies from about $10^{-2}$ to about $10^{-13}$ molar. For the measurement of a ligand concentration, it is especially advantageous to adjust in the sample a concentration of from about $10^{-3}$ to about $10^{-12}$ molar and it is especially advantagous to adjust in the sample a concentration of from about $10^{-4}$ to about $10^{-10}$ molar. Higher ligand concentrations can be measured after dilution of the original sample.

The measurement takes place at particular pH values which can extend from about 3 to 12. Usually, they lie in the range of from about 5 to about 10 and preferably in a pH range of from about 6 to about 9. For the achievement and maintenance of the pH value during the measurement, there can be used various buffers, for example borate, phosphate, carbonate or tris buffer. Which buffer is used is not decisive for the present invention. The choice depends, in the first place, upon the antibody used and upon the ligand which is to be determined, as well as upon the fluorescence labelling used.

The FPIA method is preferably carried out at a constant temperature. Normally, the temperature can be selected from the range of about 0° to 50° C. and preferably of from about 10° to about 40° C.

The precise relationship between polarisation and concentration of a ligand or ligand analogue to be determined can be read off from a calibration curve. These are obtained by measurement of the polarisation values of solutions of different but known concentrations of appropriate substances. Unknown ligand concentrations of a sample to be investigated can then be determined from such calibration curves from a knowledge of the polarisation.

A wide field of use of the compounds of general formulae (Ia) and (Ib) according to the present invention is to be seen in their general usefulness as fluorescent labellings. Thus, for example, in immunofluorescence microscopy, proteins as antigens or whole cells can be made visible by fluorescent-labelled antibodies. In a corresponding manner, the distribution of a hapten or antigen in a cell can also be directly observed and monitored, for example under a microscope, when the compound in question is introduced into the cell in fluorescent-labelled form. In contradistinction to the above-described homogeneous fluorescence immunoassay, the fluorescent properties of the resorufin derivative hereby do not change.

Known coloured materials which have previously been used as fluorescent labellings include, for example, fluoresceins, such as fluorescein isothiocyanate, and rhodamine dyes, such as Texas Red. However, as previously stated, fluoresceins have the disadvantage that they fluoresce at relatively low wavelengths. Furthermore, as is known from experience, the yield of the coupling reaction to the carrier in question is mostly small and, in addition, the colour stability of the coupling products is poor. This also applies to rhodamine dyes. Precisely with regard to this point, the compounds of general formulae (Ia) and (Ib) according to the present invention display distinct advantages over the fluorescent labellings known from the prior art. They fluoresce at long wavelengths with a good colour stability and can be prepared in good yields from compounds of general formulae (IIa) and (IIb) and appropriate coupling components.

The compounds of general formulae (IIa) and (IIb) according to the present invention can, of course, also be used for labelling substances in processes other than the above-mentioned fluorescence immunological processes. Thus, the labelling of a component of another complex-forming system is possible with these reactive resorufin compounds. By complex-forming systems are hereby to be understood all those combinations of substances which, on the basis of specific interaction forces, are able to form complexes. Known combinations include, for example, hormone/specific receptor, biotin-/avidin, carbohydrate derivative/lectin and the like. For example, proteins labelled with biotin can be determined by means of a coupling product from avidin and a reactive compound of general formula (IIa) or (IIb) according to the present invention. A further advantageous field of use of compounds of general formulae (Ia) and (Ib) according to the present invention is in the determination of a component of the lectin/carbohydrate derivative system.

Fluorescent-labelled latex particles find use in the sorting of cells in a "fluorescent activated cell sorter". Such particles can also be readily fluorescent labelled, for example by the reaction of latex particles containing hydroxyl, sulphhydryl, amino or also carboxyl or sulphonic acid groups with reactive resorufin compounds of general formulae (IIa) and (IIb).

Compounds of general formulae (Ia) and (Ib) can also be advantageously used for the determination of enzymes. For this purpose, a resorufin derivative of general formula (IIa) or (IIb) can be bound to a substrate which can be split by the enzyme to be determined. This coupling product is also a compound of general formula (Ia) or (Ib) according to the present invention. After reaction of the resorufin-labelled substrate with the enzyme and separation of the fission products and unreacted substrate, the activity of the enzyme can be determined. For example, a reactive resorufin derivative of general formula (IIa) or (IIb) can be bound to a glycopeptide and the coupling product hereby obtained used as a substrate for the detection of endoglucosidase activity. Labelling with dansyl compounds is known for the determination of endoglucosidases (see Iwase et al., Anal. Biochem., 113, 93–95/1981). In comparison with such compounds, resorufin derivatives are characterised by an especially high sensitivity.

The following Examples, which are given for the purpose of illustrating the present invention, show the fundamental possibility of labelling low and high molecular compounds and the use thereof.

EXAMPLE 1

Resorufin-4-carboxylic Acid
3-(1-diphenylhydantoinylethylcarbonyl)-piperazide a) Resorufin-4-carboxylic Acid 16 g. Nitrosoresorcinol, 15.5 g. 2,6-dihydroxybenzoic acid and 8.6 g. pyrolusite are suspended in 200 ml. methanol and cooled to 0° C. 10.6 ml. concentrated sulphuric acid are then added dropwise thereto and the reaction mixture is further stirred for 2 hours at ambient temperature. The precipitated red resazurin-4-carboxylic acid is filtered off, washed with methanol and dried.

The resazurin derivative is taken up in 200 ml. water and 50 ml. 25% aqueous ammonia solution and filtered. 50 g. zinc dust are added portionwise to the blue filtrate, with ice cooling, and the reaction mixture is then allowed to warm up to ambient temperature. The course of the reduction can easily be monitored by thin layer chromatography (elution agent: methanol/ethyl acetate 1:1 v/v; silica gel TLC plates). The reaction solution is filtered and the filtrate is then acidified with glacial acetic acid and a little concentrated hydrochloric acid. The precipitated resorufin-4-carboxylic acid is filtered off and dried in a vacuum over phosphorus pentoxide. The yield is 16.33 g.

Rf (silica gel; elution agent: n-butanol/glacial acetic acid/water 4:1:1 v/v/v)=0.4.

b) N,O,O-Triacetyldihydroresorufin-4-carboxylic Acid 12.9 g. Resorufin-4-carboxylic acid are taken up in 30 ml. glacial acetic acid and 30 ml. acetic anhydride, mixed with 27.6 g. stannous chloride and stirred for 1 hour at 80° C. The reaction mixture is then poured on to 600 ml. ice water, stirred for 1 hour and the precipitate is filtered off. After drying, the solid material is taken up in 500 ml. acetone. It is then filtered with suction and the filtrate is evaporated to give, after drying, 11.3 g. of product.

$^1$H-NMR (D$_6$-DMSO): δ=2.24, 2.26 and 2.29 (each s, 9H); 6.94 (dd, J=8.5 and 2.2 Hz, 1H); 6.98 (d, J=2.2 Hz, 1H); 7.04 (d, J=9 Hz, 1H); 7.61 (d, J= 8.5 Hz, 1H); 7.67 ppm (d, J=9 Hz, 1H).

Rf (silica gel; elution agent: chloroform/methanol/- glacial acetic acid 9:1:0.1 v/v/v)=0.46.

c) N,O,O-Triacetyldihydroresorufin-4-carboxylic Acid Chloride 38.5 g. of the triacetate described in Example 1b) are mixed with 54 ml. oxalyl chloride and cooled to 0° C. A drop of dimethylformamide is added thereto and the reaction mixture is allowed to warm up to ambient temperature. The educt thereby dissolves with the evolution of gas. The reaction mixture is evaporated to dryness in a vacuum, taken up three times with, in each case, 200 ml. amounts of dry methylene chloride and again evaporated to dryness. The yield is 41 g.

d) N-BOC-piperazine 12.61 g. N-Benzhydrylpiperazine (EMKA Chemie) are taken up in 100 ml. 1,4-dioxan/water (3:1 v/v) and 12.0 g. di-tert.-butyl dicarbonate dissolved in 50 ml. 1,4-dioxan are added dropwise thereto. After stirring for 30 minutes, 50 ml. water are added dropwise thereto, filtered and the precipitate dried. Yield: 16.2 g. N-BOC-N'-benzhydrylpiperazine.

Rf (silica gel; elution agent: chloroform/methanol/- glacial acetic acid 9:1:0.1 v/v/v)=0.92.

7 g. N-BOC-N'-benzhydrylpiperazine are taken up in 100 ml. ethyl acetate and 5 ml. glacial acetic acid. It is hydrogenated in the presence of 0.3 g. palladium on active charcoal, thereafter filtered off from the catalyst and the filtrate evaporated to dryness. The residue is mixed with 100 ml. water and 20 ml. 1N hydrochloric acid and filtered. The filtrate is extracted twice with ethyl acetate and the aqueous phase then rendered basic with aqueous sodium hydroxide solution. The oily product which separates out is extracted with dichloromethane. After drying with anhydrous sodium sulphate and evaporating, there are obtained 3.2 g. N-BOC-piperazine in the form of an oil which, after a few days, crystallises completely. Rf (silica gel; elution agent: chloroform/methanol/glacial acetic acid 9:1:0.1 v/v/v)=0.05; becomes blue with ninhydrin.

e) N,O,O-Triacetyldihydroresorufin-4-carboxylic Acid N'-BOC-piperazide

A solution of 13.8 g. N-BOC-piperazide in 50 ml. dichloromethane is added dropwise at 0° C. to 25 g. of the acid chloride described in Example 1c) and 17.3 ml. triethylamine in 450 ml. dichloromethane. The reaction mixture is stirred for 1 hour without cooling, then shaken out three times with water and the organic phase is evaporated. The yield is 36.0 g.

Rf (silica gel; elution agent: chloroform/methanol/- glacial acetic acid 9:1:0.1 v/v/v)=0.64.

f) N-Acetyldihydroresorufin-4-carboxylic acid N'-BOC-piperazide 34.3 g. of the triacetate described in Example 1e) and 17.1 g. sodium sulphite are stirred for 1 hour at 60° C. in 500 ml. 1,4-dioxan/water (1:1 v/v). The reaction mixture is subsequently evaporated and the residue is taken up in ethyl acetate, filtered off from insoluble salts and chromatographed on 2 liters of silica gel (elution agent: ethyl acetate/dichloromethane 4:1 v/v; as soon as the product is eluted, change over to pure ethyl acetate). The yield is 14 g. Rf (silica gel; elution agent: ethyl acetate/dichloromethane 4:1 v/v)=0.28.

g) Resorufin-4-carboxylic acid N'-BOC-piperazide 5 g. of the N-acetyl compound obtained in Example 1f) are dissolved in 200 ml. methanol and 600 ml. water. 1.8 g. Sodium hydrogen carbonate and 10.7 ml. 1N aqueous sodium hydroxide solution are added thereto, followed by 14 g. potassium ferricyanide. After stirring for 30 minutes at ambient temperature, the pH is adjusted to 5. The product precipitates out and is filtered off with suction. The yield is 2.72 g. Rf (silica gel; elution agent: chloroform/methanol/glacial acetic acid 9:1:0.1 v/v/v)=0.28.

h) Resofurin-4-carboxylic acid piperazide trifluoroacetate 1 g. of the BOC derivative obtained in Example 1 g) is left to stand for 15 minutes in 20 ml. trifluoroacetic acid. The reaction mixture is then evaporated, the residue is digested with diethyl ether and the product is filtered off. Yield 0.96 g. Rf (silica gel; elution agent: chloroform/methanol/glacial acetic acid 9:1:0.1 v/v/v)=0.02.

i) Coupling of resorufin-4-carboxylic Acid Piperazide with 3-(1-diphenylhydantoinyl)-propionic Acid N-hydroxysuccinimide Ester 191 mg. of the piperazide trifluoroacetate obtained in Example 1 h) and 210 mg. 3-(1-diphenylhydantoinyl)-propionic acid N-hydroxysuccinimide ester (prepared from diphenylhydantoin sodium salt and ethyl 3-bromopropionate analogously to Cook et al., Res. Communications in Chemical Pathology and Pharmacology, 5, 767/1973) are stirred for 15 hours in 20 ml. dioxan and 20 ml. 0.1M potassium phosphate buffer (pH 8.5). The precipitated product is filtered off and the filtrate is evaporated and chromatographed on silica gel RP18 (elution agent: isopropanol), additional product thereby being obtained. The product obtained is crystallised from ethyl acetate/methanol to give a total of 250 mg. of coupling product. Rf (silica gel; elution agent: chloroform/methanol/glacial acetic acid 9:1:0.1 v/v/v)=0.61.

$^1$H-NMR (D$_6$-DMSO): δ=2.6-2.8 (m, 2H); 3.0-3.8 (m, 10H); 6.74 (d, J=2.2 Hz, 1H); 6.82 (d, J=9.5 Hz, 1H); 6.91 (dd, J=9.5 and 2.2 Hz); 7.25-7.33 (m, 10H); 7.55 and 7.66 ppm (each d, J=9.5 Hz, 2H).

UV/VIS (0.1M potassium phosphate buffer, pH 7.5)=λ$_{max}$=576.8 nm.

Fluorescence emission: λ$_{max}$=592 nm.

EXAMPLE 2

Coupling of resorufin-4-carboxylic Acid Piperazide with 3-(1-diphenylhydantoinyl)-acetic Acid N-hydroxysuccinimide Ester Analogously to Example 1 i), from 365 mg. resorufin-4-carboxylic acid piperazide trifluoroacetate and 339 mg. 3-(1-diphenylhydantoinyl)-acetic acid N-hydroxysuccinimide ester, there are obtained 210 mg. of the desired product.

Rf (silica gel; elution agent: n-butanol/glacial acetic acid/water 4:1:1 v/v/v)=0.82.

$^1$H-NMR (D$_6$-DMSO): δ=3.2-4.5 (m, 10H); 6.60 (d, J=2.4 Hz, 1H); 6.71 (d, J=9.5 Hz, 1H); 6.80 (dd, J=9.05 and 2.4 Hz, 1H); 7.39 ("s", 10H); 7.52 (d, J=9.5 Hz, 1H); 7.61 (d, J=9.0 Hz, 1H); 9.65 ppm (s, 1H).

UV/VIS (0.1M potassium phosphate buffer, pH 8.0): λ$_{max}$=575.4 nm.

Fluorescence emission: λ$_{max}$=592 nm.

EXAMPLE 3

Coupling of Resorufin-4-carboxylic Acid Piperazide with N-BOC-L-thyroxine-N-hydroxysuccinimide Ester Analogously to Example 1 i), from 212 mg. resorufin-4-carboxylic acid piperazide trifluoroacetate and 419 mg. N-BOC-L-thyroxine-N-hydroxysuccinimide ester, there are obtained 320 mg. of the desired product.

Rf (silica gel; elution agent: chloroform/methanol/glacial acetic acid 9:1:0.1 v/v/v)=0.58.

The N-BOC-L-thyroxine-N-hydroxysuccinimide ester is obtained in the following manner:

a) N-BOC-thyroxine

A solution of 10 g. (12.5 mMole) L-thyroxine sodium salt monohydrate in a mixture of 300 ml. dioxan/water (2:1 v/v) and 15 ml. 1N aqueous sodium hydroxide solution is mixed with 3 g. (13.75 mMole) di-tert.-butyl dicarbonate ((BOC)$_2$O) and stirred for 2 hours at ambient temperature with the exclusion of light. The pH is adjusted to 2 with 2M potassium hydrogen sulphate solution, the solution is extracted with ethyl acetate and the ethyl acetate extract is washed with water, dried over anhydrous sodium sulphate and evaporated. The solid residue is triturated with petroleum ether, filtered off with suction and dried in a desiccator. Yield 9.45 g. (86% of theory).

Rf (silica gel; elution agent: chloroform/ligroin/acetic acid 6:3:1 v/v/v)=0.6.

b) N-BOC-Thyroxine-N-hydroxysuccinimide Ester 1.2 g. (9.5 mMole) N-hydroxysuccinimide is added to a solution of 8.8 g. L-BOC-thyroxine in 200 ml. ethyleneglycol dimethyl ether. The solution is cooled to 10° C. and mixed dropwise with a solution of 2.3 g. (9.9 mMole) dicyclohexylcarbodiimide in 40 ml. ethyleneglycol dimethyl ether. After stirring for 2 hours at ambient temperature, the precipitated dicyclohexylurea is filtered off with suction and the filtrate evaporated in a vacuum at 40° C. The residue is triturated with isopropanol and filtered off with suction. The product is dried at ambient temperature in a desiccator. Yield 9.19 g. (94% of theory) (total yield referred to thyroxine=81%).

Rf (HPTLC-RP 18; elution agent: nitromethane/ethanol 9:1 v/v)=0.8; or (HPTCL-RP 18; elution agent: acetonitrile/water 8:2 v/v)=0.6.

$^1$H-NMR (D$_6$-DMSO): δ=1.36 (s, 9H); 2.81 (s, 4H); 2.9-3.2 (m, 2H); 4.5-4.9 (m, 1H); 7.03 (s, 2H); 7.63 (d, J=9 Hz, 1H); 7.90 (s, 2H); 9.2 (s, 1H).

EXAMPLE 4

Coupling of resorufin-4-carboxylic Acid Piperazide with 3-O-[3-(N-succinimidoxycarbonyl)-propyl]oestradiol Analogously to Example 1 i), from 212 mg. resorufin-4-carboxylic acid piperazide trifluoroacetate and 220 mg. 3-O-[3-(N-succinimidyloxycarbonyl)-propyl]oestradiol, there are obtained 295 mg. of the desired product.

Rf (silica gel; elution agent: chloroform/methanol/glacial acetic acid 9:1:0.1 v/v/v)=0.58.

3-O-[3-(N-succinimidoxycarbonyl)-propyl]oestradiol is obtained in the usual manner from 3-O-carboxypropyloestradiol (obtained from oestradiol and bromobutyric acid analogously to Lübke et al., in Immunologische Teste für niedermolekulare Wirkstoffe, pub. G. Thieme Verlag, Stuttgart, p. 94) N-hydroxysuccinimide in the presence of dicyclohexylcarbodiimide.

EXAMPLE 5

Coupling of Resorufin-4-carboxylic Acid Piperazide with N-[3-(N-succinimidoxycarbonyl)-propyl]phenobarbital Analogously to Example 1 i), from 212 mg. resorufin-4-carboxylic acid piperazide trifluoroacetate and 205 mg. N-[3-(N-succinimidoxycarbonyl)-propyl]phenobarbital, there are obtained 220 mg. of the desired product.

Rf (silica gel; elution agent: chloroform/methanol/glacial acetic acid 9:1:0.1 v/v/v)=0.45

N-[3-(N-succinimidoxycarbonyl)-propyl]-phenobarbital is obtained in the usual manner from phenobarbital-1-butyric acid (T. Nistikawa et al., Clin. Chim. Acta, 91, 59/1979) and N-hydroxysuccinimide in the presence of dicyclohexylcarbodiimide.

EXAMPLE 6

Coupling of Resorufin-4-carboxylic Acid Piperazide with Theophylline-7-propionic acid N-hydroxysuccinimide Ester Analogously to Example 1 i), from 212 mg. resorufin-4-carboxylic acid piperazide trifluoroacetate and 175 mg. theophylline-7-propionic acid N-hydroxysuccinimide ester, there are obtained 200 mg. of the desired product.

Rf (silica gel; elution agent: chloroform/methanol/glacial acetic acid 9:1:0.1 v/v/v)=0.44.

Theophylline-7-propionic acid N-hydroxysuccinimide ester is obtained in the usual manner from theophylline-7-propionic acid (T. Nistikawa et al., Chem. Pharm. Bull, 27, 893/1979) and N-hydroxysuccinimide in the presence of dicyclohexylcarbodiimide.

EXAMPLE 7

Coupling of N-(4-resorufincarbonyl)-sarcosine-N'-hydroxysuccinimide Ester with 1-(2-aminoethyl)diphenylhydantoin a) N,O,O-Triacetyldihydroresorufin-4-carboxylic Acid (tert.-butoxycarbonylmethyl)-methylamide 10 g. of the acid chloride described in Example 1 c) are reacted with sarcosine tert.-butyl ester analogously to Example 1 e). Yield 7.5 g.

Rf (silica gel; elution agent: chloroform/methanol/glacial acetic acid 9:1:0.1 v/v/v)=0.77.

b) N-Acetyldihydroresorufin-4-carboxylic Acid (tert.-butoxycarbonylmethyl)-methylamide 7.5 g. of the product according to Example 7a) are deacetylated analogously to Example 1f). Yield 5.2 g.

Rf (silica gel; elution agent: chloroform/methanol/glacial acetic acid 9:1:0.1 v/v/v)=0.56.

c) Resorufin-4-carboxylic Acid (tert.-butoxycarbonylmethyl)methylamide 4.5 g. of the product according to Example 7b) are reacted analogously to Example 1 g). Yield 2.6 g.

Rf (silica gel; elution agent: chloroform/methanol/glacial acetic acid 9:1:0.1 v/v/v)=0.64.

d) Resorufin-4-carboxylic Acid(carboxymethyl)methylamide 0.55 g. of the product according to Example 7c) is left to stand for 1 hour at ambient temperature in 6 ml. trifluoroacetic acid. The reaction mixture is then evaporated to dryness and the residue is triturated with diethyl ether and filtered. Yield 0.45 g.

Rf (silica gel; elution agent: chloroform/methanol/glacial acetic acid 9:1:0.1 v/v/v)=0.11.

e) N-(4-Resorufinylcarbonyl)-sarcosine-N'-hydroxysuccinimide ester 200 mg. of the product according to Example 7d) are stirred for 4 hours in 40 ml. tetrahydrofuran with 72 mg. N-hydroxysuccinimide and 138 mg. dicyclohexylcarbodiimide. The precipitated urea is filtered off, the filtrate is evaporated and the residue is chromatographed on silica gel RP 18 (elution agent: nitromethane/ethanol 4:1 v/v). Yield 150 mg.

Rf (silica gel RP 18; elution agent: nitromethane/ethanol 4:1 v/v)=0.79.

f) Coupling of N-(4-resorufinylcarbonyl)-sarcosine N'-hydroxysuccinimide ester with 1-(2-aminoethyl)diphenylhydantoin 125 mg. of the N-hydroxysuccinimide ester obtained in Example 7e) are stirred with 90 mg. 1-(2-aminoethyl)-diphenylhydantoin in 40 ml. dioxan/potassium phosphate buffer (pH 8.5) (1:1 v/v) for 1 hour. The dioxan is then evaporated off, ammonia is added until the colour change is complete and then filtered and the product is precipitated from the filtrate with hydrochloric acid. Yield 110 mg.

Rf (silica gel; elution agent: n-butanol/glacial acetic acid/water 4:1:1 v/v/v)=0.78.

UV/VIS (0.1M potassium phosphate buffer, pH 8.0): $\lambda_{max}$=575 nm.

Fluorescence emission: $\lambda_{max}$=592 nm.

EXAMPLE 8

Resorufin-4-carboxylic acid 2-(1-diphenylhydantoinyl)ethylamide a) N,O,O-Triacetyldihydroresorufin-4-carboxylic Acid 2-(1-diphenylhydantoinyl)-ethylamide Analogously to Example 1e), 1.37 g. 1-(2-aminoethyl)-diphenylhydantoin is reacted with 1.2 g. N,O,O-triacetyldihydroresorufin-carboxylic acid chloride, 1.9 g. of product being obtained as a slightly coloured foam.

b) Resorufin-4-carboxylic acid 2-(1-diphenylhydantoinyl)ethylamide

The product obtained in Example 8a) is deacetylated analogously to Examples 1f) and 1g). From 1.9 g. of educt, there are obtained 600 mg. of product.

Rf (silica gel; elution agent: chloroform/methanol/glacial acetic acid 9:1:0.1 v/v/v)=0.68.

$^1$H-NMR (D$_6$-DMSO): δ=3.2–3.6 (m, 4H); 6.73 (d, J=2.2 Hz, 1H); 6.84 (d, J=9.5 Hz, 1H); 6.86 (dd, J=9.5 and 2.2 Hz, 1H); 7.2–7.4 (m, 10H); 7.62 and 7.66 (each d, J=9.5 Hz, 2H); 8.66 (t, wide, J=5 Hz, 1H); 9.58 ppm (s, 1H).

UV/VIS (0.1M potassium phosphate buffer, pH 8.0) $\lambda_{max}$=575 nm

Fluorescence emission: $\lambda_{max}$=591 nm.

EXAMPLE 9

Coupling of 6-methylresorufin-4-carboxylic Acid piperazide with 2-(1-diphenylhydantoinyl)-acetic Acid N-hydroxysuccinimide Ester a) 2-Methyl-4-nitrosoresorcinol 19.8 g. 2-Methylresorcinol and 13.4 g. potassium hydroxide are dissolved in 120 ml. ethanol and cooled to 5° C. 24 ml. Isopentyl nitrite are added dropwise thereto, the reaction mixture is stirred for 3 hours and the precipitate is filtered off with suction. The yellow solid material is stirred into 200 ml. 5N sulphuric acid, the bright yellow product thereby precipitating out. Yield 22 g.

Rf (silica gel; elution agent: chloroform/methanol/glacial acetic acid 9:1:0.1 v/v/v) = 0.53.

b) 6-Methylresazurin-4-carboxylic Acid 15.3 g. 2-Methyl-4-nitrosoresorcinol, 15.4 g. 2,6-dihydroxybenzoic acid, 8.8 g. pyrolusite and 11 ml. concentrated sulphuric acid are reacted analogously to Example 1a). Yield 28.7 g.

Rf (silica gel; elution agent: chloroform/methanol/glacial acetic acid 9:1:0.1 v/v/v) = 0.15.

c) N,O,O-Triacetyl-6-methyldihydroresorufin-4-carboxylic Acid

Analogously to Example 1b), from 10 g. 6-methylresazurin-4-carboxylic acid, 19.8 g. stannous chloride, 20 ml. acetic anhydride and 150 ml. glacial acetic acid, the triacetylated leuko compound is obtained directly. The crude product is purified by boiling out with acetone. Yield 7.3 g.

Rf (silica gel; elution agent: chloroform/methanol/glacial acetic acid 9:1:0.1 v/v/v) = 0.51.

$^1$H-NMR (D$_6$-DMSO): $\delta$ = 2.10, 2.25, 2.29, 2.33 (each s, 12H); 7.00, 7.09, 7.50 and 7.74 ppm (each d, J = 8.8 Hz, 4H).

d) N,O,O-Triacetyl-6-methyldihydroresorufin-4-carboxylic acid N'-BOC-piperazide

Analogously to Examples 1d) and 1e), from 5 g. N,O,O-triacetyl-6-methyldihydroresorufin-4-carboxylic acid, 10.7 ml. oxalyl chloride and 2 g. N-BOC-piperazine, there are obtained 3 g. of the desired product.

Rf (silica gel; elution agent: ethyl acetate) = 0.57.

e) 6-Methylresorufin-4-carboxylic acid piperazide trifluoroacetate 1 g. of the triacetyl derivatives obtained according to Example 9d) is reacted analogously to Examples 1g) and 1h). Yield 0.43 g.

f) Coupling of 6-methylresorufin-4-carboxylic acid piperazide with 2-(1-diphenylhydantoinyl)-acetic acid N-hydroxysuccinimide Ester 222 mg. of the compound obtained in Example 9e) are reacted with 200 mg. 2-(1-diphenylhydantoinyl)acetic acid N-hydroxysuccinimide ester. Yield 250 mg. UV/VIS (0.1M potassium phosphate buffer, pH 8.0): $\lambda_{max}$ = 584 nm.

Fluorescence emission: $\lambda_{max}$ = 600 nm.

EXAMPLE 10

Coupling of 9-hydroxy-5-benzo[a]phenoxazone-8-carboxylic Acid Piperazide with 2-(1-diphenylhydantoinyl)-acetic Acid N-hydroxysuccinimide Ester a) 9-Hydroxy-5-benzo[a]phenoxazone-8-carboxylic Acid 12-oxide 2.84 g. 1,3-dihydroxy-4-nitrosonaphthalene, 2.31 g. 2,6-dihydroxybenzoic acid, 1.29 g. pyrolusite and 1.6 ml. concentrated sulphuric acid are reacted analogously to Example 1a). Yield 2.8 g.

Rf (silica gel; elution agent: n-butanol/glacial acetic acid/water 4:1:1 v/v/v) = 0.63 b) 12-Acetyl-5,9-diacetoxybenzo[a]phenoxazone-8-carboxylic Acid

Analogously to Example 9c), from 2.4 g. 9-hydroxy-5-benzo[a]phenoxazone-8-carboxylic acid 12-oxide, there is obtained 1.8 g. of the triacetylated dihydroxy compound.

Rf (silica gel; elution agent: chloroform/methanol/glacial acetic acid 9:1:0.1 v/v/v) = 0.31.

c) 12-Acetyl-5,9-diacetoxybenzo[a]phenoxazine-8-carboxylic acid N'-BOC-piperazide 1.6 g. of the triacetyl compound obtained according to Example 10b) is reacted with oxalyl chloride and N-BOC-piperazine analogously to Example 9d). Yield 1.2 g.

$^1$H-NMR (CDCl$_3$): $\delta$ = 1.49 (s, 9H); 2.12, 2.27, 2.46 (each s, 12H); 3.0–3.9 (m, 8H); 7.03 (d, J = 9 Hz, 1H); 7.16–7.94 ppm (m, 6H).

d) 9-Hydroxy-5-benzo[a]phenoxazone-8-carboxylic Acid N'-BOC-piperazide

Analogously to Example 1 f), from 0.93 g. of the triacetyl compound of Example 10 c), there is obtained 0.51 g. of the desired product.

Rf (silica gel; elution agent: chloroform/methanol/glacial acetic acid 9:1:0.1 v/v/v) = 0.69.

e) 9-Hydroxy-5-benzo[a]phenoxazone-8-carboxylic Acid piperazide Trifluoroacetate From 0.5 g. of the BOC-protected compound described in Example 10 d), there is obtained 0.5 g. of the desired product analogously to Example 1 h).

Rf (silica gel; elution agent: chloroform/methanol/glacial acetic acid 9:1:0.1 v/v/v) = 0.02.

f) Coupling of 9-hydroxy-5-benzo[a]phenoxazone-8-carboxylic Acid Piperazide with 2-(1-diphenylhydantoinyl)-acetic acid N-hydroxysuccinimide Ester From 50 mg. of the piperazide prepared according to Example 10 e) and 150 mg. 2-(1-diphenylhydantoinyl)acetic acid N-hydroxysuccinimide ester, there are obtained 70 mg. of the desired product analogously to Example 1 i).

Rf (silica gel; elution agent: chloroform/methanol/glacial acetic acid 9:1:0.1 v/v/v) = 0.57.

UV/VIS (0.1M potassium phosphate buffer, pH 8.0): $\lambda_{max}$ = 560 nm.

Fluorescence emission: $\lambda_{max}$ = 6.51 nm.

$^1$H-NMR (D$_6$-DMSO): $\delta$ = 3.0–4.5 (m, 10H); 6.37 (s, 1H); 6.80 (d, J = 8 Hz, 1H); 7.2–7.35 (m, 10H); 7.35–8.0

(m, 3H); 8.10 (dd, J=8 and 2 Hz, 1H); 8.56 (dd, J=8 and 2 Hz, 1H); 9.60 ppm (s, 1H).

EXAMPLE 11

8-Ethylresorufin-4-carboxylic Acid (1-diphenylhydantoinylmethylcarbonyl)-piperazide a) 6-Ethyl-4-nitrosoresorcinol

Analogously to Example 9 a), from 7.5 g. ethylresorcinol, 4.5 g. potassium hydroxide and 8 ml. isopentyl nitrite, there is obtained 6-ethyl-4-nitrosoresorcinol as a yellow solid material. Yield 7.5 g.

Rf (silica gel; elution agent: chloroform/methanol/glacial acetic acid 9:1:0.1 v/v/v)=0.37.

b) 8-Ethylresorufin-4-carboxylic Acid

Analogously to Example 1 a), from 7.4 g. 6-ethyl-4-nitrosoresorcinol, 6.8 g. 2,6-dihydroxybenzoic acid, 3.9 g. manganese dioxide and 5 ml. concentrated sulphuric acid, there are obtained, after reduction with 8 g. zinc dust, 9.5 g. of the desired product.

Rf (silica gel; elution agent: chloroform/methanol/glacial acetic acid 9:1:0.1 v/v/v)=0.05.

c) N,O,O-Triacetyl-8-ethyldihydroresorufin-4-carboxylic Acid N'-BOC-piperazide Analogously to Example 1 b), from 7.7 g. 8-ethylresorufin-4-carboxylic acid, 15.4 g. stannous chloride, 30 ml. glacial acetic acid and 15.3 ml. acetic anhydride, there is obtained the desired crude product which is directly further worked up analogously to Example 1 c) to give the acid chloride and this is further directly worked up analogously to Example 1 e) to give the BOC-piperazide. Yield 4 g.

Rf (silica gel; elution agent: chloroform/methanol/glacial acetic acid 9:1:0.1 v/v/v)=0.86.

d) 8-Ethylresorufin-4-carboxylic acid N'-BOC-piperazide

From 4 g. N,O,O-triacetyl-8-ethyldihydroresorufin-4-carboxylic acid N'-BOC-piperazide there is obtained, analogously to Examples 1 f) and 1 g), the corresponding carboxylic acid N'-BOC-piperazide. Yield 0.5 g.

Rf (silica gel; elution agent: chloroform/methanol 4:1 v/v)=0.67.

e) 8-Ethylresorufin-4-carboxylic Acid Piperazide Trifluoroacetate 330 mg. of the appropriate BOC-piperazide are left to stand for 1.5 hours in 35 ml. dichloromethane/trifluoroacetic acid. After evaporation, the residue is digested with diethyl ether, filtered off with suction and dried. Yield 350 mg.

Rf (silica gel; elution agent: butanol/glacial acetic acid/water 4:1:1 v/v/v)=0.33.

f) Reaction with 2-(1-diphenylhydantoinyl)-acetic acid N-hydroxysuccinimide ester Analogously to Example 1 i), from 325 mg. 8-ethylresorufin-4-carboxylic acid piperazide trifluoroacetate and 435 mg. 2-(1-diphenylhydantoinyl)-acetic acid N-hydroxysuccinimide ester, there are obtained 120 mg. of the desired product.

Rf (silica gel; elution agent: chloroform/methanol/glacial acetic acid 9:1:0.1 v/v/v)=0.43.

$^1$H-NMR (D$_6$-DMSO): δ=1.15 (t, J=7.2 Hz, 3H); 2.52 (q, J=7.2 Hz, 2H); 3.1–4.0 (m, 8H); 4.25–4.45 (m, 2H); 6.42 (s, broad, 1H); 6.94 (d, J=9.0 Hz, 1H); 7.3–7.5 (m, 11H); 7.68 (d, J=9.0 Hz, 1H); 9.54 (s, 1H); 11.2 ppm (s, broad, 1H).

UV/VIS (0.1M potassium phosphate buffer, pH 8.0): λ$_{max}$=575 nm.

Fluorescence emission: λ$_{max}$=598 nm.

EXAMPLE 12

8-Chlororesorufin-4-carboxylic acid (1-diphenylhydantoinylmethylcarbonyl)-piperazide a) 8-Chlororesazurin-4-carboxylic Acid

From 17.3 g. 4-chloro-6-nitrosoresorcinol (prepared according to Plampin and Cain, J. Med. Chem., 6, 247/1963), 15.4 g. 2,6-dihydroxybenzoic acid, 8.6 g. pyrolusite and 10.7 ml. concentrated sulphuric acid, there is obtained, analogously to Example 1 a), 8-chlororesorufin-4-carboxylic acid. Yield 17.1 g.

Rf (silica gel; elution agent: butanol/glacial acetic acid/water 4:1:1 v/v/v)=0.58.

b) N,O,O-Triacetyl-8-chlorodihydroresorufin Carboxylic Acid 16.3 g. 8-Chlororesazurin-4-carboxylic acid and 18.9 g. stannous chloride are heated to 80° C. for 30 minutes in 100 ml. glacial acetic acid/acetic anhydride (1:1 v/v) and then poured into 500 ml. ice water. The mixture is stirred for 2 hours, filtered off from precipitate and dried over Sicapent. The solid material obtained is taken up in 500 ml. acetone and filtered off from undissolved residues. The filtrate is evaporated and, after drying, there are obtained 12.3 g. of the desired product.

Rf (silica gel; elution agent: chloroform/methanol/glacial acetic acid 9:1:0.1 v/v/v)=0.39.

$^1$H-NMR (D$_6$-DMSO): δ=2.25 (s, 3H); 2.33 ("s", 6H); 7.16 (d, J=8.8 Hz, 1H); 7.30 (s, 1H); 7.76 (d, J=8.8 Hz, 1H); 7.90 ppm (s, 1H).

c) 8-Chlororesorufin-4-carboxylic acid N'-BOC-piperazide

Analogously to Examples 1 b), 1 c) and 1 e), from 5 g. N,O,O-triacetyl-8-chlorodihydroresorufin-4-carboxylic acid, there is obtained 0.8 g. of the desired product.

Rf (silica gel; elution agent: chloroform/methanol/glacial acetic acid 9:1:0.1 v/v/v)=0.7.

d) 8-Chlororesorufin-4-carboxylic Acid Piperazide Trifluoroacetate

From 0.8 g. of the BOC-protected compound of Example 12 c), there is obtained, analogously to Example 1 h), 0.81 g. of the desired product.

Rf (silica gel; elution agent: chloroform/methanol/glacial acetic acid 9:1:0.1 v/v/v)=0.07.

e) Coupling of 8-chlororesorufin-4-carboxylic Acid piperazide with 2-(1diphenylhydantoinyl)-acetic Acid N-hydroxysuccinimide Ester Analogously to Example 1 i), from 400 mg. 8-chlororesorufin-4-carboxylic acid piperazide trifluoroacetate and 410 mg. 2-(1-diphenylhydantoinyl)-acetic acid N-hydroxysuccinimide ester, there is obtained the desired product. Yield 150 mg.

Rf (silica gel; elution agent: chloroform/methanol/glacial acetic acid 9:1:0.1 v/v/v)=0.38.

UV/VIS (0.1M potassium phosphate buffer, pH 8.0): λ$_{max}$=581 nm

Fluorescence emission: λ$_{max}$=597 nm.

EXAMPLE 13

Coupling of 8-chlororesurifin-1-carboxylic Acid Piperazide with Theophylline-7-propionic Acid 2-aminoethylamide a) 8-Chlororesorufin-4-carboxylic Acid 8.7 g. 4-Chloro-6-nitrosoresorcinol and 7.71 g. 3,5-dihydroxybenzoic acid are dissolved in 200 ml. methanol, 4.8 g. of pyrolusite are added thereto at 0° C. and portionwise 5.3 ml. concentrated sulphuric acid. The reaction mixture is stirred for 2 hours at ambient temperature, filtered and ammonia added thereto up to the colour change to blue and 200 ml. water. The solution is filtered, the filtrate is mixed with 25 ml. concentrated aqueous ammonia solution and 20 g. zinc dust, while cooling with ice, and thereafter, without further cooling, stirred for about 15 minutes. 200 mg. active charcoal are added thereto, filtered, the filtrate is acidified to pH 2 and the precipitated resorufin derivative is then centrifuged off. Yield 3.9 g.

Rf (silica gel; elution agent: n-butanol/glacial acetic acid/water 4:1:1 v/v/v)=0.88.

b) N,O,O-Triacetyl-8-chlorodihydroresorufin-1-Carboxylic Acid

Analogously to Example 1 b), from 3.5 g. 8-chlororesorufin-1-carboxylic acid there are obtained 3.2 g. of the desired product.

Rf (silica gel; elution agent: chloroform/methanol/-glacial acetic acid 9:1:0.1 v/v/v)=0.43.

c) 8-Chlororesorufin-1-carboxylic Acid Piperazide Trifluoroacetate

From 3 g. of the triacetyl compound prepared according to Example 11 b), there is obtained 1.4 g. of the desired product analogously to Examples 1 c) to 1 h).

Rf (silica gel; elution agent: chloroform/methanol/-glacial acetic acid 9:1:0.1 v/v/v)=0.08.

d) Coupling of 8-chlororesorufin-1-carboxylic Acid Piperazide with theophylline-7-propionic Acid 2-aminoethylamide Analogously to Example 8, from 420 mg. N,O,O-triacetyl-8-chlorodihydroresorufin-1-carboxylic acid piperazide and 300 mg. theophylline-7-propionic acid 2-aminoethylamide, there are obtained 190 mg. of the desired product.

EXAMPLE 14

Labelling of Immunoglobulin G with N-(4-resorufinylcarbonyl)-sarcosine N'-hydroxysuccinimide Ester 100 mg. Human IgG are dissolved in 10 ml. 0.1M potassium phosphate buffer (pH 8.0) and mixed with 5 mg. N-(4-resorufinylcarbonyl)-sarcosine N'-hydroxysuccinimide ester (cf. Example 7 e)). The reaction mixture is left to stand for 12 hours at ambient temperature and then chromatographed on Ultrogel ACA 202 (LKB). The labelled protein is thereby eluted before the free low molecular weight resorufin. The degree of labelling is determined by means of extinction measurement. It is 3, i.e. per molecule of IgG, there are bound 3 molecules of the resorufin derivative.

EXAMPLE 15

Labelling of Immunoglobulin G with N-(4-resorufinylcarbonyl)-piperidine-4-carboxylic Acid N'-hydroxysuccinimide Ester a) N-(4-Resorufinylcarbonyl)-piperidine-4-carboxylic Acid 2.0 g of the N,O,O-triacetyldihydroresorufin-4-carboxylic acid chloride described in Example 1 c) are reacted analogously to Example 1 e) with 0.9 g. methyl piperidine-4-carboxylate hydrochloride, deacetylated analogously to Examples 1 f) and 1 g) and oxidised and then saponified with an aqueous solution of sodium hydroxide to give N-(4-resorufincarbonyl)-piperidine-4-carboxylic acid. Yield 0.9 g.

Rf (silica gel RP-18; elution agent: nitromethane/ethanol 4:1 v/v)=0.44.

UV/VIS (0.1M potassium phosphate buffer, pH 8.5): $\lambda_{max} = 576.2$ nm.

b) N-(4-Resorufinylcarbonyl)-piperidine-4-carboxylic Acid N'-hydroxysuccinimide Ester Analogously to Example 7 e) from 200 mg. N-(4-resorufinylcarbonyl)-piperidine-4-carboxylic acid, 240 mg. N-hydroxysuccinimide and 468 mg. dicyclocarbodiimide, there are obtained 190 mg. of the desired product.

Rf (silica gel RP-18; elution agent: nitromethane/ethanol 4:1 v/v)=0.7.

IR (KBr pressed body): 3415 (m, broad), 1814 (w), 1773 (m), 1734 (s), 1626 (m), 1214 (m) cm$^{-1}$.

c) Labelling of Rabbit IgG with N-(4-resorufinylcarbonyl)-piperidine-4-carboxylic Acid N'-hydroxysuccinimide Ester 10 mg. Rabbit IgG, dissolved in 1 ml. 0.1M potassium phosphate buffer (pH 8.5), are mixed with 100 μl. of a solution of 1.9 mg. N-(4-resorufinylcarbonyl)-piperidine-4-carboxylic acid N-hydroxysuccinimide ester in 1 ml. 1,4-dioxan and left to stand for 2 hours at ambient temperature. This corresponds to a ratio of 6.4 mole of resorufin derivative per 1 mole of rabbit IgG.

After chromatography on ACA 202 (eluent: 0.1M potassium phosphate buffer; pH 8.5), there is obtained a protein fraction which has an absorption ratio $A_{578}/A_{280}=0.97$, corresponding to a degree of loading of 3.4 mole resorufin per mole of IgG.

When, in an analogous experiment, 10 mg. rabbit IgG are mixed with 20 μl. of a solution of the activated resorufin, there is obtained, in the case of 1.05 mole of available coloured material per mole of IgG, a degree of loading of 0.8.

The absorption maximum of the resorufin-labelled IgG is 578 nm. The solution fluoresces strongly with a bright red colour.

If a solution of the resorufin-labelled IgG is exposed to daylight for a month, the fluorescence intensity drops to 59% of the original value, whereas an analogously prepared IgG labelled with fluorescein isothiocyanate decreases to 16% and an IgG labelled with Texas Red decreases to 12%.

EXAMPLE 16

Diphenylhydantoin determination in human serum by means of FPIA

1950 µl. 0.1M sodium phosphate buffer (pH 7.8) are mixed with 5 µl. of sample (1), 25 µl. of antibody solution (2) and 25 µl. diphenylhydantoin-resorufin solution (3). After incubation for 5 minutes at 37° C., the fluorescence polarisation is measured (excitation wavelength: 578 nm, emission wavelength 594 nm, measurement apparatus; fluorescence spectrometer 650-10S, Hitachi).

1) Sample: human donor serum made up with a known amount of diphenylhydantoin. For the production of a calibration curve, there is used human donor serum which contains diphenylhydantoin in concentrations of:
a) 2.5 µg./ml.
b) 5 µg./ml.
c) 10 µg./ml.
d) 20 µg./ml.
e) 40 µg./ml.

2) Antibody solution: 450 µg. antibody/ml. 0.1M sodium phosphate buffer (pH 7.8).

The antibodies are obtained in a conventional manner by immunising sheep with diphenylhydantoin which is bound to bovine serum albumin via glutardialdehyde. The antiserum is purified by ammonium sulphate precipitation and chromatography on DEAE-cellulose.

3) Diphenylhydantoin-resorufin solution ($10^{-6}$M): diphenylhydantoin-resorufin conjugate of Example 1 i) in 0.1M sodium phosphate buffer (pH 7.8).

The measurement results, which are obtained with diphenylhydantoin solutions 1a)-1e), are illustrated in FIG. 1 of the accompanying drawings in which the diphenylhydantoin concentrations of the samples (µg./ml.) are plotted against the measured polarisation values (mP).

With the help of such a calibration curve, there can also be determined the diphenylhydantoin concentration in samples with an unknown content of diphenylhydantoin.

A comparable calibration curve is also obtained when, instead of the above-used diphenylhydantoin conjugate from Example 1 i), there is, in each case, used the diphenylhydantoin conjugate of Examples 2, 7, 8 or 10f).

EXAMPLE 17

Determination of an endoglycosidase activity with resorufin-high mannose glycopeptide a) Labelling of high mannose glycopeptide with N-(4-resorufinylcarbonyl)-sarcosine N'-hydroxysuccinimide ester 50 mg. High mannose glycopeptide (prepared according to Huang et al., Carbohydrate Res., 13, 127-137/1970) are mixed with 10 ml. 0.1M potassium phosphate buffer (pH 8.0), the solution subsequently being adjusted to a pH of 8.0. 25 mg. N-(4-resorufinylcarbonyl)-sarcosine N'-hydroxysuccinimide ester, dissolved in 3 ml. dioxan, are added thereto and, after 1 hour, the same amount of coloured material-N-hydroxysuccinimide ester in 3 ml. dioxan are added thereto. The reaction mixture is stirred for 14 hours at ambient temperature, the dioxan is then evaporated off in a vacuum and the residue diluted with water to 70 ml. and thereafter with buffer A (0.02M tris HCl, 2 mM magnesium chloride, 2 mM manganese chloride, 2 mM calcium chloride; pH 7.2) to 140 ml. The pH is adjusted to 7.2 with aqueous ammonia solution. Precipitate thereby formed is centrifuged off. The supernatant is applied to a Con A-Sepharose column (1×15 cm.) and the free coloured material washed out with buffer A. As soon as the flow-through is no longer red, a first fraction of resorufin-high mannose glycopeptide is eluted with 2% methylmannoside in buffer A as eluent (about 100 ml.). Thereafter, a second fraction is eluted with 2% aqueous methylmannoside. Both fractions are dialysed against water and lyophilised. Both fractions can be used for the determination of the endoglycosidase activity described hereinafter under b).

b) Determination of Endoglycosidase Activity

Resorufin-high mannose glycopeptide is incubated in an appropriate buffer with endoglycosidase, for example endoglycosidase H, and citrate buffer (pH 5.5) (sample 1). Parallel thereto, a sample is used which does not contain endoglycosidase but which is otherwise identical (sample 2). After incubation, both samples are mixed with Con A-Sepharose and shaken in order to bind resorufin-high mannose glycopeptide. Resorufin-labelled peptide, in which the sugar part is split off by the enzyme activity, is not bound. After 15 minutes, the Con A-Sepharose is centrifuged off, the supernatant is adjusted to pH 7.5 and the fluoresence is measured (excitation, for example, 550 nm, emission $\lambda_{max}$=595 nm). The difference between sample 1 and the blank (sample 2) gives the amount of split resorufin-high mannose glycopeptide and is thus a measure of the enzyme activity.

It will be understood that the specification and examples are illustrative but not limitative of the present invention and that other embodiments within the spirit and scope of the invention will suggest themselves to those skilled in the art.

What is claimed is:

1. A colored or fluorescent resorufin derivative designated resorufin-4-carboxylic acid piperazide or 8-chlororesorufin-4-carboxylic acid piperazide.

2. A colored or fluorescent resorufin derivative designated N-(4-resorufinylcarbonyl)-piperidine-4-carboxylic acid-N'-hydroxysuccinimide ester.

3. A colored or fluorescent resorufin derivative designated 6-methylresorufin-4-carboxylic acid piperazide trifluoroacetate.

4. A colored or fluorescent resorufin derivative designated 8-ethylresorufin-4-carboxylic acid (1-dephenylhydantoinylmethylcarbonyl)-piperazide.

5. A colored or fluorescent resorufin derivative designated 8-chlororesorufin-4-carboxylic acid piperazide trifluoroacetate.

6. A colored or fluorescent resorufin derivative designated 8-chlororesorufin-1-carboxylic acid piperazide trifluoroacetate.

7. A colored or fluorescent resorufin derivative designated resorufin-4-carboxylic acid (tert-butoxycarbonylmethyl)-methylamide.

8. A colored or fluorescent resorufin derivative designated 9-hydroxy-benzophenoxazone-8-carboxylic acid piperazide trifluoroacetate.

* * * * *